United States Patent
Cudak et al.

(10) Patent No.: US 9,721,453 B2
(45) Date of Patent: Aug. 1, 2017

(54) CONTROLLING THE SPREAD OF PATHOGENS

(71) Applicant: International Business Machines Corporation, Armonk, NY (US)

(72) Inventors: Gary D. Cudak, Wake Forest, NC (US); Christopher J. Hardee, Raleigh, NC (US); Sarbajit K. Rakshit, Kolkata (IN); Adam Roberts, Moncure, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/838,449

(22) Filed: Aug. 28, 2015

(65) Prior Publication Data
US 2017/0061773 A1    Mar. 2, 2017

(51) Int. Cl.
*G08B 23/00* (2006.01)
*G08B 21/24* (2006.01)
*A41D 1/00* (2006.01)

(52) U.S. Cl.
CPC ........... *G08B 21/245* (2013.01); *A41D 1/002* (2013.01)

(58) Field of Classification Search
CPC ........... D06F 39/003; D06F 2058/2861; D06F 33/02; D06F 58/28; D06F 93/00; D06F 2058/2883; D06F 2202/10; D06F 2210/00; D06F 39/005; D06F 3/04842; D06F 9/5055; D06F 3/0481; G06K 19/00; G06K 19/06037
USPC ........ 340/573.1, 505, 539.11, 539.12, 539.1, 340/568.1, 572.1–572.9, 286.07, 5.9–5.92
See application file for complete search history.

(56) References Cited

U.S. PATENT DOCUMENTS

| | | | | |
|---|---|---|---|---|
| 5,313,393 A | * | 5/1994 | Varley | G06Q 10/087 194/205 |
| 7,142,118 B2 | * | 11/2006 | Hamilton | G06Q 50/22 209/3.3 |
| 7,898,407 B2 | * | 3/2011 | Hufton | G01S 1/70 222/23 |
| 8,320,634 B2 | * | 11/2012 | Deutsch | A61B 90/94 382/103 |
| 8,653,970 B2 | | 2/2014 | Hazzani | |

(Continued)

FOREIGN PATENT DOCUMENTS

CN    203325028 U    12/2013

OTHER PUBLICATIONS

Cudak et al., "Controlling the Spread of Pathogens", U.S. Appl. No. 14/838,830, filed Aug. 28, 2015.

(Continued)

*Primary Examiner* — Daniel Previl
(74) *Attorney, Agent, or Firm* — Patterson + Sheridan, LLP

(57) ABSTRACT

Systems, methods, and computer program products to perform an operation comprising receiving, based on a unique identifier of an identification device in a room, clinical information of a first patient present in the room, receiving a unique identifier from an identification device associated with a garment worn by a health care professional in the room, receiving a history of the garment based on the unique identifier, and upon determining that the history of the garment violates a predefined rule, outputting a notification of the violation.

13 Claims, 4 Drawing Sheets

(56) References Cited

U.S. PATENT DOCUMENTS

| | | | | |
|---|---|---|---|---|
| 2009/0243833 | A1* | 10/2009 | Huang | G06F 19/323 340/505 |
| 2009/0267776 | A1* | 10/2009 | Glenn | G08B 21/245 340/573.1 |
| 2011/0007950 | A1* | 1/2011 | Deutsch | A61B 90/94 382/111 |
| 2014/0104062 | A1 | 4/2014 | Weiner | |
| 2015/0109442 | A1* | 4/2015 | Derenne | G08B 21/245 348/143 |

OTHER PUBLICATIONS

Tiyu Zhao et al., "Applications for Radio-frequency Identification Technology in the Perioperative Setting", AORN Journal, vol. 99, Issue 6, pp. 764-781, Jun. 2014. <http://dx.doi.org/10.1016/j.aorn.2013.07.022>.

"Hospital-acquired infection", Wikipeida, pp. 1-8, retrieved Apr. 15, 2015, <http://en.wikipedia.org/wiki/Hospital-acquired_infection>.

JoNel Aleccia, "Hosptial garb harbors nasty bacteria, new study says", NBCNEWS.com, updated Aug. 31, 2011, retrieved Apr. 15, 2015, 3 pages <http://www.nbcnews.com/id/44334682/ns/health-infectious_diseases/t/hospital-garb-harbors-nasty-bacteria-new-study-says/>.

NXP Semiconductors, "RFID- and NFC-Enabled Smart Washing Machine Detects Fabric, Supports Remote Maintenance", Feb. 29, 2012, retrieved Apr. 15, 2015, 2 pages. <http://www.nxp.com/news/press-releases/2012/02/rfid-and-nfc-enabled-smart-washing-machine-detects-dabric--supports-remote-maintenance.html>.

Kimaldi Electronics, "Control of hospital clothing with RFID tags in hospitals", retrieved Apr. 15, 2015, 2 pages. <http://www.kimaldi.com/kimaldi_eng/solutions/radiofrequency_rfid/control_of_hospital_clothing_with_rfid_tags_in_hospitals>.

TAGSYS RFID e-connecting goods, RFID systems and solutions by the TAGSYS RFID company, retrieved Apr. 15, 2015, © TAGSYS—2015. <http://www.tagsysrfid.com/en-EN/home>.

* cited by examiner

CONTROLLING THE SPREAD OF PATHOGENS

BACKGROUND

The present invention relates to healthcare, and more specifically, to techniques to control the spread of pathogens.

In healthcare settings such as hospitals, health care professionals move from room to room where they are exposed to different patients having different health conditions. Some of the patients may have contagious infections, which can spread from patient to patient via the health care professionals. For example, pathogens from a first patient may be carried on a doctor's lab coat or scrubs to a second patient, exposing the second patient (among others) to further illness if the doctor's clothing is not properly washed.

SUMMARY

Embodiments disclosed herein provide systems, methods, and computer program products to perform an operation comprising receiving, based on a first identifier of a first identification device in a room, clinical information of a first patient present in the room, receiving a second identifier from a second identification device associated with a garment worn by a health care professional in the room, receiving a history of the garment based on the second unique identifier, and upon determining that the history of the garment violates a predefined rule, outputting a notification of the violation.

DETAILED DESCRIPTION

Figure 1:
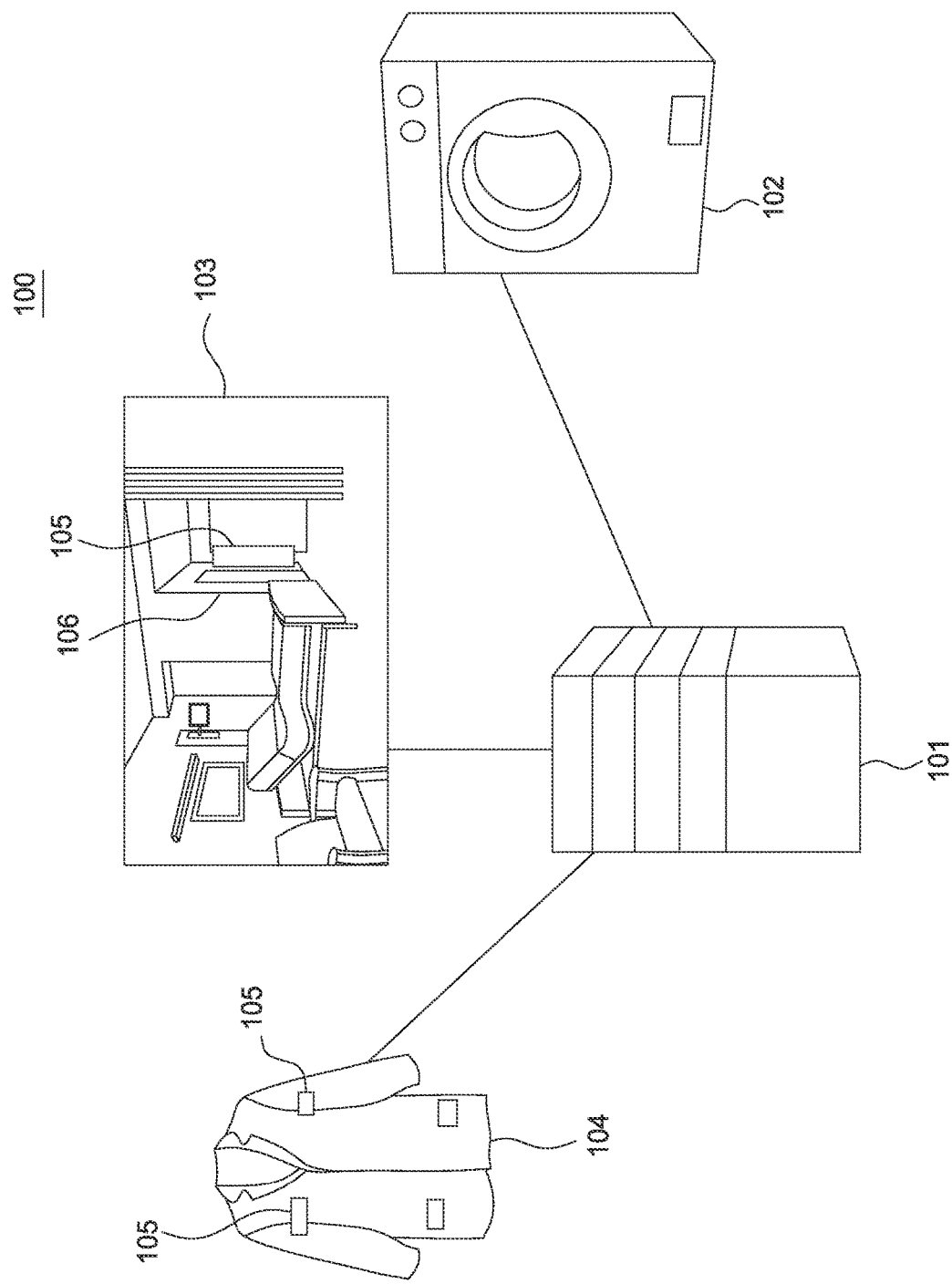
FIG. 1 illustrates techniques to control the spread of pathogens, according to one embodiment.

Embodiments disclosed herein use historical information about garments worn by health care professionals to determine whether the location of any given garment violates a predefined rule. To this end, the garments may be tagged with unique identifiers (such as radio frequency identifier (RFID) chips) that are associated with historical information. The historical information may indicate when the garments were washed (and by what washing method) and what types of pathogens the garments have been exposed to. If a garment has been exposed to a pathogen, and the garment has not been properly washed subsequent to the exposure, embodiments disclosed herein may output a notification to prevent the pathogen from spreading.

For example, when a doctor enters a patient's hospital room, RFID scanners may scan the RFID tags on garments worn by the doctor. Based on the RFID tags, embodiments disclosed herein may retrieve a history for garments. The history may specify a set of previous washes of the garments, which may include timestamps of each washing of the garments and the methods by which the garments were washed. The history of the garments may also indicate which patients (and any associated pathogens or other conditions of the patients) the garments have previously been exposed to. Embodiments disclosed herein leverage this information to determine whether the doctor's presence in the room violate any rules intended to prevent the spread of pathogens. For example, a rule may specify that garments exposed to patients having influenza must be washed prior to the garments being exposed to any other patients. If, for example, the history of a lab coat indicates the doctor wore the lab coat while attending to a patient who has influenza, and the garment has not been washed since the exposure to influenza, embodiments disclosed herein may issue an alert to notify the doctor that he or she should not enter the room of another patient. For example, when the doctor enters the next patient's room, embodiments disclosed herein may trigger an alert on the doctor's smart phone indicating that the doctor needs to change the lab coat before entering the room.

Generally, when a doctor is exposed to a patient (such as by entering the patient's room, or being in an operating room with the patient), embodiments disclosed herein may use the RFID identifiers to create an association between the garments worn by the doctor (and/or the doctor individually) and the patient. In addition, the patient's medical history may be referenced (using, for example, an RFID tag in the patient's room that is associated with the patient) to associate the garments with any pathogens or other medical conditions the patient may have. One or more rules may specify requirements for washing the garments subsequent to any such exposure. When the RFID tags on the doctor's garments are scanned in a different room (or around a different patient), embodiments disclosed herein may determine whether the rules for washing the garment have been satisfied. If the rules have not been satisfied, embodiments disclosed herein may trigger an alert to prevent the doctor from possibly exposing another person to the illness.

In addition, the rules may specify constraints that are based on locations. For example, assume there is a particular part of a hospital designated for people with highly infectious communicable diseases. A doctor entering that area may be identified and registered in the monitoring system, regardless of which particular patient or patients the doctor interacts with. An alert may then be triggered when the doctor subsequently leaves the designated area and attempts to enter another area of the hospital. As used herein, the term "health care professional" refers to any person interacting with patients, including, without limitation, doctors, dentists, nurses, physical therapists, support staff, janitorial staff, and the like. While specific locations, such as hospital rooms, operating rooms, or other areas where patients may interact with health care professional are used as examples herein, any such use is for illustrative purposes, and should not be considered limiting of the disclosure.

FIG. 1 illustrates techniques to control the spread of pathogens, according to one embodiment. Generally, the block diagram 100 depicts interrelated components configured to control the spread of pathogens by enforcing proper sanitation and washing rules for garments worn by health care professionals. As shown, a central server 101 may be communicably coupled with garments 104, washing stations 102, and patient locations 103 (such as patient rooms). Generally, a garment may be any body-worn item capable of transferring pathogens. In particular, garments include clothing such as pants, shirts, coats, scrubs, hats, shoes, etc. Garments may further include articles patients are exposed to, such as bed sheets, towels, and the like. As shown, the garments 104 include one or more identification devices 105. The identification devices 105 may be any hardware configured to transmit a unique identifier to a receiver. Examples of identification devices include as RFID tags, Bluetooth® modules, global positioning system (GPS) modules, near field communication (NFC) modules and the like. When a garment 104 is washed at a washing station 102 (or otherwise sanitized), a record of the washing event may be associated with the identification devices 105 of the garment, and stored in the server 101. The record of the washing event may include a timestamp of the washing and any methods used to wash the garment 104 (such as temperature of water, cleansing agents used, chemical cleaning methods, and the like). In one embodiment, the record may be automatically created upon detecting that the garment 104 has entered the washing station 102 (i.e., is with insufficient proximity for a card reader located in the washing station to read the identification device on the garment). In another embodiment, a human operator may be required to explicitly create the record of the washing event (e.g., by manually scanning the garment and entering the desired washing history via a terminal).

As shown, the patient room 103 includes a reader device 106, and an identification device 105 that may be associated with a patient (not pictured). The reader device 106 may be any device configured to receive a unique identifier from an identification device, such as an RFID reader, GPS receiver, Bluetooth receiver or NFC device. When a person (such as a doctor) wearing a garment 104 enters the room 103, the reader 106 may detect the identification devices 105 in the garment. In a particular embodiment, detection occurs once the reader 106 and the identification devices 105 are within some predefined distance of one another (i.e., within communication range of each other). The reader 106 may transmit the unique identifiers of the identification devices 105 to the server 101, which may identify the washing history of the garment, and any patients the garment was previously exposed to. The server 101 may then identify one or more rules (not pictured) related to a medical condition (or pathogen) the previous patients may have had. If the server 101 determines that the washing history (and/or the exposure history) would violate a rule as to the patient in the room 103, the server 101 may generate and output a notification that the doctor should not enter the room 103 wearing the garment 104. The notification may be sent to a mobile device used by the doctor (not pictured), or outputted by a speaker, monitor, or other device in the room 103 (or proximate thereto). Generally, the notification may be of any type.

For example, if the server 101 determines that the garment 104 was previously exposed to a bacterium, the server 101 may reference a rule for washing the garment 104 which indicates any garment exposed to the bacterium must be washed in hot water (for example, at 80 degrees Celsius). The server 101 may reference the washing history and determine that the garment 104 was exposed to the bacterium at 10:00 AM on Friday, Apr. 17, 2015, and the garment 104 was washed at 10:30 AM on the same date. If the doctor attempts to wear the garment 104 into the room 103 at 1:00 PM on Apr. 17, 2015, the server 101 would permit the doctor to proceed with the patient visit in the room 103. However, if the 10:30 AM wash event is not detected, and the most recent wash associated with the identification devices 105 of the garment 104 occurred on Apr. 16, 2015, then the server 101 would output a notification that the garment 104 should not be worn in the room 103 to prevent the spread of the bacterium to the patient in room 103. Similarly, if the most recent wash record indicates that the garment was washed in water at 70 degrees Celsius, the server 101 would output a notification that the garment 104 should not be worn in the room 103.

In addition to electromagnetic signaling technology, embodiments disclosed herein may further leverage visual identification techniques. For example, the garments may be provisioned with an element identifiable by a camera system. The element may be, for example, a physical object secured in a prominent location on the garment. The element could be a Universal Product Code (UPC), Quick Response (QR) code, or a reflective material that produces a unique spectral signature. In such embodiments, a camera system may track the movement of these garments.

Figure 2:
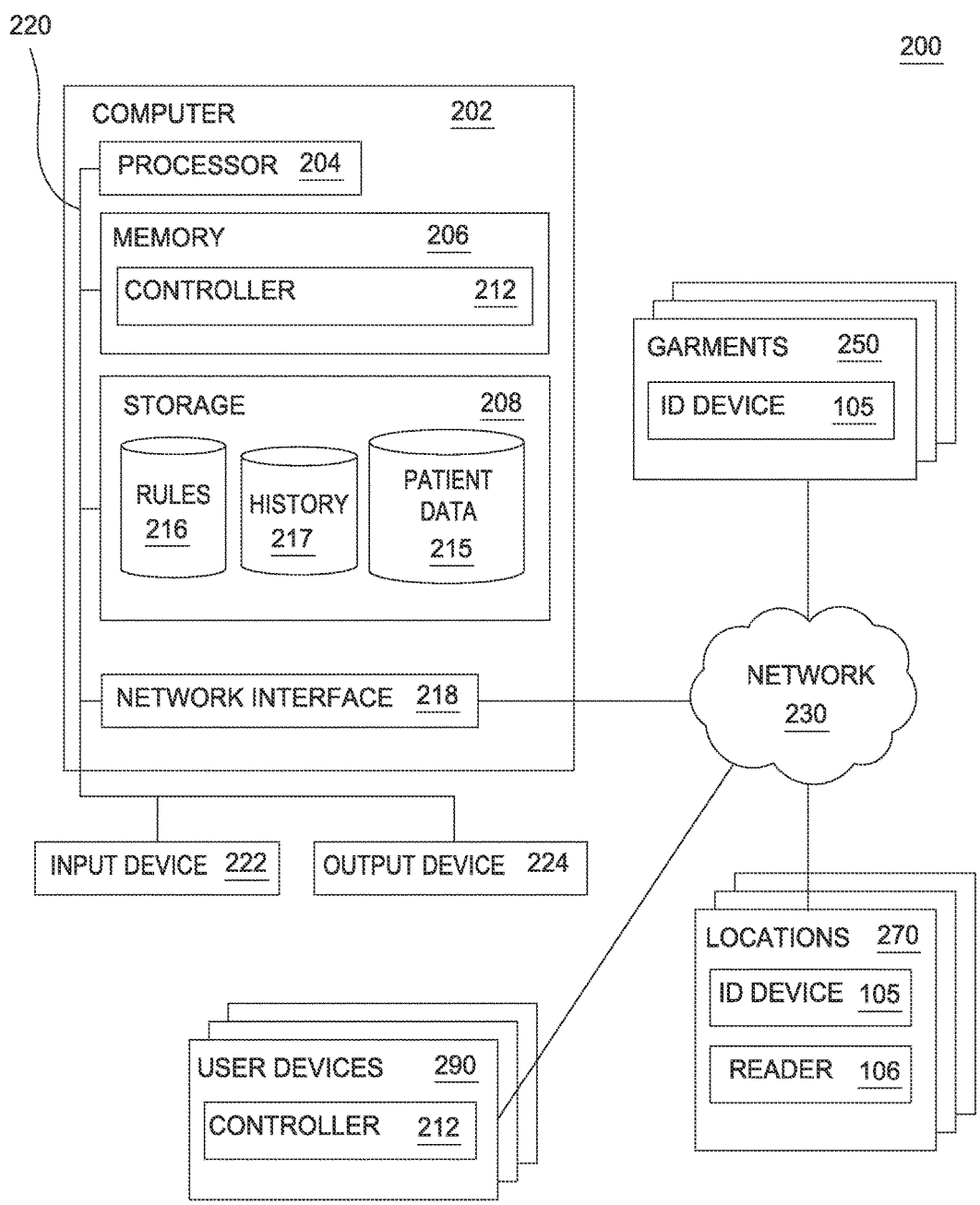
FIG. 2 illustrates a system configured to control the spread of pathogens, according to one embodiment.

FIG. 2 illustrates a system 200 configured to control the spread of pathogens, according to one embodiment. The networked system 200 includes a computer 202. The computer 202 may also be connected to other computers via a network 230. In general, the network 230 may be a telecommunications network and/or a wide area network (WAN). In a particular embodiment, the network 230 is the Internet.

The computer 202 generally includes a processor 204 which obtains instructions and data via a bus 220 from a memory 206 and/or a storage 208. The computer 202 may also include one or more network interface devices 218, input devices 222, and output devices 224 connected to the bus 220. The computer 202 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 204 is a programmable logic device that performs instruction, logic, and mathematical processing, and may be representative of one or more CPUs. The network interface device 218 may be any type of network communications device allowing the computer 202 to communicate with other computers via the network 230.

The storage 208 is representative of hard-disk drives, solid state drives, flash memory devices, optical media and the like. Generally, the storage 208 stores application programs and data for use by the computer 202. In addition, the memory 206 and the storage 208 may be considered to include memory physically located elsewhere; for example, on another computer coupled to the computer 202 via the bus 220.

The input device 222 may be any device for providing input to the computer 202. For example, a keyboard and/or a mouse may be used. The input device 222 represents a wide variety of input devices, including keyboards, mice, controllers, and so on. Furthermore, the input device 222 may include a set of buttons, switches or other physical device mechanisms for controlling the computer 202. The output device 224 may include output devices such as monitors, touch screen displays, and so on.

As shown, the memory 206 contains the controller 112, which is an application generally configured to control the spread of pathogens. More specifically, the controller 112 determines whether garments 250 worn by health care professionals violate any of the rules 216. When a reader 106 at a given location 270 reads an identification (ID) device 105 of a garment 250, the controller 212 may receive a unique identifier of the ID device 105 via the network 230. The controller 212 may then reference the history 217 of the ID device 105 to determine when the associated garment 250 was previously washed, and any patients that the garment 250 was exposed to. The controller 212 may further identify any associated pathogens or other illnesses associated with the patient in the patient data 215. If the controller 212 determines that the garment 250 being in the location 270 violates one of the rules 216, the controller 212 may output a notification that the garment 250 needs to be removed from the location 270. The garments 250 may be any type of clothing, footwear, accessories, and the like.

For example, a nurse may wear scrubs with an associated ID device 105 to a first patient's hospital room. A reader 106 in the first patient's room may identify the ID device 105 affixed to the scrubs, and store an indication that the scrubs were present in the first patient's room in the history 217. The first patient may be identified by a respective ID device 105 that is associated with the patient. If the nurse subsequently goes to a second patient's room in the hospital, the reader 106 in the second hospital room may detect the ID device 105 of the nurse's scrubs, and transmit the unique identifier of the ID device 105 of the scrubs to the controller 212. The controller 212 may use the unique identifier of the ID device 105 of the scrubs to determine, based on the history data 217, that the nurse was previously in the first patient's room. The controller 212 may then reference the patient data 215 to determine what conditions or pathogens the first patient has, and identify any rules 216 associated with the identified pathogens or conditions the first patient has. For example, if the patient data 215 indicates the first patient has chicken pox, the controller 212 may identify a rule 216 indicating any garments exposed to chicken pox must be washed in a chemical bath to kill the virus. The controller 212 may also search the history data 217 to determine whether the scrubs were washed in the chemical bath subsequent to the nurse's visit to the first patient. If the history 217 does not have a record indicating the scrubs were washed in a chemical bath, the controller 212 may send a notification to the nurse's user device 212 that the nurse must remove the scrubs prior to entering the second patient's room.

As shown, the storage 208 includes the rules 216, the history data 217, and patient data 215. The rules 216 include any type of rule to prevent the spread of pathogens or illnesses. For example, the rules 216 may specify washing instructions that are mapped to specific pathogens. The washing instructions may specify washing methods, timing of washes, and the like. Similarly, the rules 216 may specify conditions or pathogens which different patients (or classes of patients) cannot be exposed to. The history 217 includes a history of an ID device 105 affixed to each garment 250. The history 217 therefore includes an indication of each location 270 where each garment 250 was worn, a timestamp of each washing of a garment 250 (and by what method the garment was washed), and identifiers of any patients the garment 250 was exposed to. The patient data 215 may include any information about a patient, including associated rules 216, medical history, current conditions, current pathogens, current illnesses, and the like.

The user devices 290 may be any type of computing device, such as a laptop, tablet computer, smart phone, pager, desktop computer, and the like. As shown, the user devices 290 execute an instance of the controller 212, which is configured to output notifications on the user devices 290 when a rule 216 is violated. The locations 270 may be any location in a health care facility, such as patient examination rooms, operating rooms, reception areas, and the like. The locations 270 include a reader 106 that is configured to read or receive unique identifiers from ID devices 105. For example, a washing room 270 may have a reader 106 that identifies each garment 250 that is washed by staff. When staff washes a garment 250, an entry specifying the ID device 105 of the garment 250, a timestamp, and washing method may be created in the history 217. Each location 270 may include an ID device 105 that may be associated with a patient (such as when the location 270 is a hospital room, and the ID device 105 is associated with the patient staying in the room).

Figure 3:
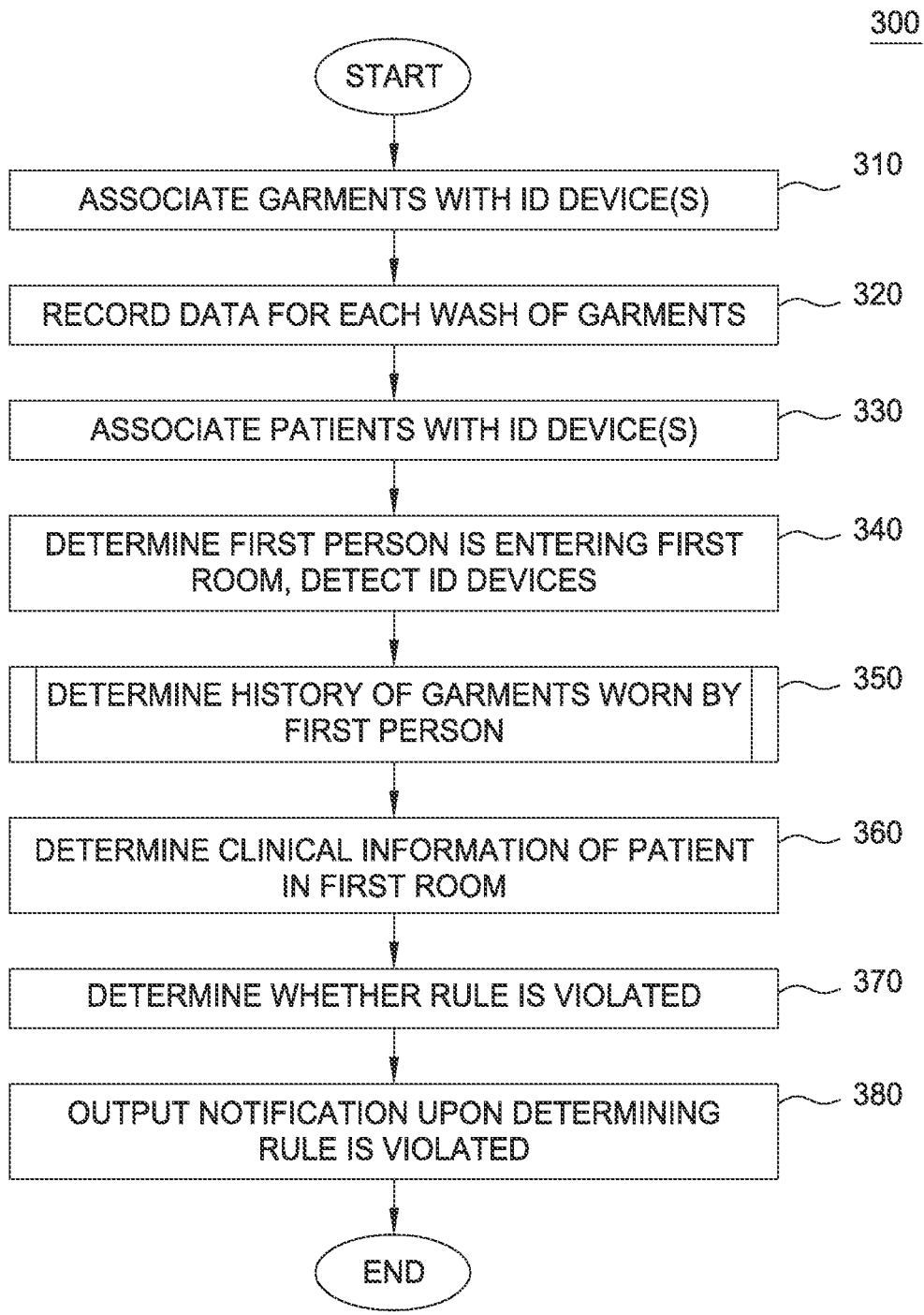
FIG. 3 is a flow chart illustrating a method to control the spread of pathogens, according to one embodiment.

FIG. 3 is a flow chart illustrating a method 300 to control the spread of pathogens, according to one embodiment. The method 300 begins at step 310, where garments are associated with one or more ID devices 105. For example, an RFID chip may be embedded into the collar of lab coats, scrubs, and the like. At step 320, data reflecting each time a garment is washed may be stored in the history 217. The recorded data may include a timestamp indicating when the garment was washed and what techniques were used to wash the garment. At step 330, patients may be associated with an ID device 105. For example, an RFID chip in a patient's room may be associated with the patient (and the patient's records in the patient data 215). At step 340, an ID device reader 106 may determine that a first person is entering a first room by receiving the unique identifier from the ID device 105 associated with a garment of clothing worn by the first person. At step 350, the controller 212 may determine a history of the garments worn by the first person based on the detected ID devices 105. The controller 212 may, for example, identify records in the history data 217 specifying the unique identifier of the ID device 105 worn by the first person. The records in the history data 217 may indicate washing history and patients that the garments were exposed to. At step 360, the controller 212 may determine the clinical information of a patient in the first room by referencing the patient data 215. Doing so allows the controller 212 to identify any relevant pathogens, conditions, and/or rules 216 associated with the first patient. In at least one embodiment, if the rules 216 are not specified in the patient data 215, the controller 212 may identify rules 216 based on the pathogens or other conditions of the patient. At step 370, the controller 212 may determine whether a rule 216 is violated. For example, if a rule 216 indicates a garment must be washed after being exposed to a virus, the controller 212 may check the history 217 to determine whether the garment was washed after being exposed to the virus. At step 380, the controller 212 may, upon determining that a rule is violated, output a notification that the rule is violated. For example, if the controller 212 determines that the lab coat of the first person has not been washed since being exposed to the virus, the controller 212 may output the notification that the lab coat should not be worn in the first room.

Figure 4:
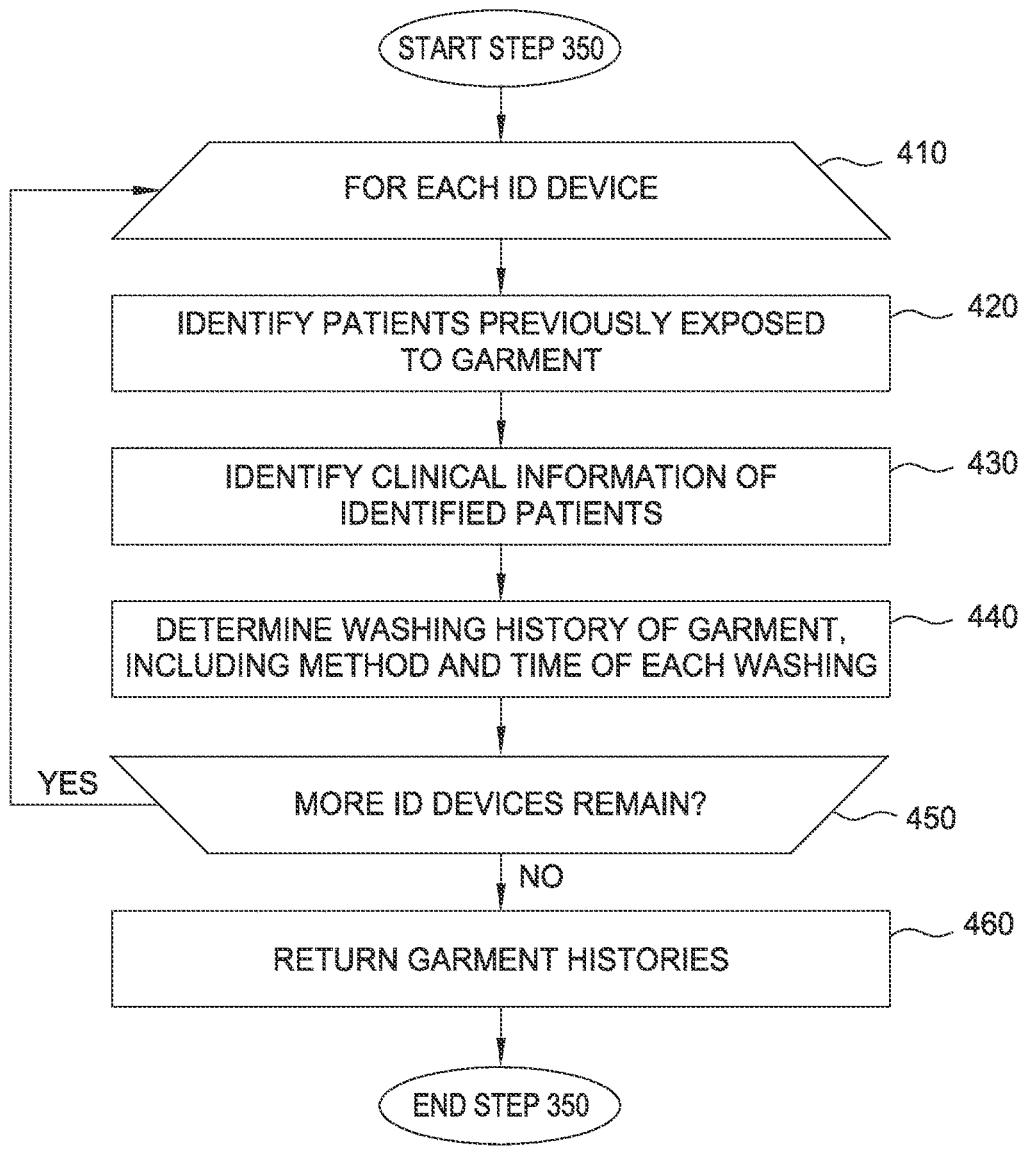
FIG. 4 is a flow chart illustrating a method to determine a history of garments, according to one embodiment.

FIG. 4 is a flow chart illustrating a method 400 corresponding to step 360 to determine a history of garments, according to one embodiment. As shown, the method begins at step 410, where the controller 212 executes a loop including steps 420-450 for each ID device 105 detected at step 340. At step 420, the controller 212 may identify each patient that was previously exposed to the garment based on entries in the history data 217 associated with the current ID device 105. At step 430, the controller 212 may identify clinical information for each patient identified at step 420 from the patient data 215. At step 440, the controller 212 may determine the washing history of each garment, which may include the method and time of each washing. In at least one embodiment, the controller 212 may impose date and/or time restrictions on the data searched for at steps 420, 430, and/or 440 to limit the size of data sets returned by the respective data stores. At step 450, the controller 212 may determine whether any more ID devices 105 remain. If more ID devices 105 were identified at step 340, the method returns to step 410 to determine the history of the garment. If no more ID devices 105 remain, the method proceeds to step 460, where the garment histories are returned.

Advantageously, embodiments disclosed herein provide precise tracking of garments, the patients the garments are exposed to, the pathogens or medical conditions of the patients, and the washing history of each garment. If a rule related to washing the garment is violated, embodiments disclosed herein output warning notifications to prevent the spread of pathogens to other people.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the controller 212 could execute on a computing system in the cloud and emit notifications when rules 216 are violated in a health care environment. In such a case, the controller could receive data regarding garment exposure to patients and store history data 217 at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A system, comprising:
one or more computer processors; and
a memory containing a program which when executed by the processors performs an operation comprising:
receiving clinical information of a first patient present in a room, wherein the clinical information comprises a disease type of the first patient and is received from a digital record of the first patient, the digital record having been accessed based on a first identifier of a first identification device in the room;
receiving a second identifier from a second identification device associated with a garment worn by a health care professional in the room;
receiving a history of the garment based on the second identifier; and
upon determining that the history of the garment violates a predefined rule associated with the clinical information of the first patient, outputting a notification of the violation.

2. The system of claim 1, wherein the history of the garment comprises: (i) a set of patients previously exposed to the garment, (ii) clinical information of each of the patients in the set of patients previously exposed to the garment, and (iii) a washing history of the garment, wherein the washing history specifies, for each of a plurality of washes of the garment, a respective date, time, and washing method.

3. The system of claim 1, wherein the rule comprises one of: (i) a set of medical conditions the first patient cannot be exposed to, (ii) a required method of washing the garment, and (iii) a required timing of washing the garment.

4. The system of claim 3, wherein the required method of washing the garment and the required timing of washing the garment are based on a medical condition, wherein each of a plurality of required methods of washing the garment are based on a respective medical condition, wherein each of a plurality of required washing times are based on a respective medical condition, the operation further comprising prior to receiving the clinical information:
associating the first patient with the first identifier of the first identification device in the room;
identifying the first patient based on the first identifier of the first identification device in the room; and
referencing a data store storing the digital record of the first patient using the first identifier of the first identification device wherein the first patient is of a plurality of patients having a respective digital record in the data store.

5. The system of claim 1, wherein the clinical information stored in the digital record of the first patient further comprises: (i) a pathogen type of the first patient, (ii) an allergy of the first patient, and (iii) a medical condition of the first patient.

6. The system of claim 1, where the identification devices comprise one or more of: (i) a radio frequency identification (RFID) device, (ii) a global positioning system (GPS) device, (iii) a Bluetooth device, and (iv) a near field communication (NFC) device.

7. The system of claim 1, wherein the garment was previously exposed to a second patient, the operation further comprising:
   determining, based on a digital record of the second patient, that the second patient has a first disease; and
   determining that the rule specifies that the first patient does not have the first disease and should not be exposed to the first disease, wherein outputting the notification of the violation prevents the health care professional from wearing the garment in the room of the first patient.

8. A computer program product, comprising:
   a computer-readable storage medium having computer-readable program code embodied therewith, the computer-readable program code executable by one or more computer processors to perform an operation comprising:
      receiving clinical information of a first patient present in a room, wherein the clinical information comprises a disease type of the first patient and is received from a digital record of the first patient, the digital record having been accessed based on a first identifier of a first identification device in the room;
      receiving a second identifier from a second identification device associated with a garment worn by a health care professional in the room;
      receiving a history of the garment based on the second identifier; and
      upon determining that the history of the garment violates a predefined rule associated with the clinical information of the first patient, outputting a notification of the violation.

9. The computer program product of claim 8, wherein the history of the garment comprises: (i) a set of patients previously exposed to the garment, (ii) clinical information of each of the patients in the set of patients previously exposed to the garment, and (iii) a washing history of the garment, wherein the washing history specifies, for each of a plurality of washes of the garment, a respective date, time, and washing method.

10. The computer program product of claim 8, wherein the rule comprises one of: (i) a set of medical conditions the first patient cannot be exposed to, (ii) a required method of washing the garment, and (iii) a required timing of washing the garment, the operation further comprising prior to receiving the clinical information:
    associating the first patient with the first identifier of the first identification device in the room;
    identifying the first patient based on the first identifier of the first identification device in the room; and
    referencing a data store storing the digital record of the first patient using the first identifier of the first identification device wherein the first patient is of a plurality of patients having a respective digital record in the data store.

11. The computer program product of claim 10, wherein the required method of washing the garment and the required timing of washing the garment are based on a medical condition, wherein each of a plurality of required methods of washing the garment are based on a respective medical condition, wherein each of a plurality of required washing times are based on a respective medical condition.

12. The computer program product of claim 8, wherein the clinical information stored in the digital record of the first patient further comprises: (i) a pathogen type of the first patient, (ii) an allergy of the first patient, and (iii) a medical condition of the first patient.

13. The computer program product of claim 8, where the identification devices comprise one or more of: (i) a radio frequency identification (RFID) device, (ii) a global positioning system (GPS) device, (iii) a Bluetooth device, and (iv) a near field communication (NFC) device, wherein the garment was previously exposed to a second patient, the operation further comprising:
    determining, based on a digital record of the second patient, that the second patient has a first disease; and
    determining that the rule specifies that the first patient does not have the first disease and should not be exposed to the first disease, wherein outputting the notification of the violation prevents the health care professional from wearing the garment in the room of the first patient.

* * * * *